United States Patent [19]

Bull

[11] 4,320,194

[45] Mar. 16, 1982

[54] PROCESS FOR THE PRODUCTION OF CARRIER PARTICLES FROM YEAST CELLS AND FOR PRODUCING DIAGNOSTIC AGENTS THEREFROM AND TEST KITS CONTAINING SUCH AGENTS

[75] Inventor: Frederick G. Bull, West Wellow, England

[73] Assignee: Gist-Brocades N.V., Delft, Netherlands

[21] Appl. No.: 172,992

[22] Filed: Jul. 28, 1980

[30] Foreign Application Priority Data

Jul. 30, 1979 [GB] United Kingdom ............... 26508/79

[51] Int. Cl.$^3$ ............................................ G01N 33/54
[52] U.S. Cl. ....................................... 435/7; 435/174; 435/175; 435/255; 435/810; 424/12; 23/230 B
[58] Field of Search ................... 435/7, 810, 175, 255, 435/260, 174; 424/8, 12; 23/230 B

[56] References Cited

U.S. PATENT DOCUMENTS

| | | | |
|---|---|---|---|
| 3,553,310 | 1/1971 | Cszimas et al. | 424/8 |
| 3,639,558 | 2/1972 | Cszimas et al. | 424/12 |
| 3,652,761 | 3/1972 | Weetall | 424/12 |
| 3,987,159 | 10/1976 | Spona et al. | 424/8 |
| 4,107,287 | 8/1978 | Morton et al. | 435/7 |

*Primary Examiner*—Benoit Castel
*Attorney, Agent, or Firm*—Hammond & Littell, Weissenberger and Muserlian

[57] ABSTRACT

Yeast cells are converted into carrier particles useful as carriers for proteins and other materials useful in agglutination tests by cross-linking the proteins of the cell cytoplasm followed by stabilization of the carbohydrates of the cell wall by reaction with an epoxide. The stabilized cells obtained may be dyed and may be esterified or etherified to block the hydroxyl groups in their surfaces. They may be coupled to the protein or other material by activation, e.g. with cyanuric chloride, followed by reaction with the protein or other material to produce diagnostic agents useful in test kits.

18 Claims, No Drawings

PROCESS FOR THE PRODUCTION OF CARRIER PARTICLES FROM YEAST CELLS AND FOR PRODUCING DIAGNOSTIC AGENTS THEREFROM AND TEST KITS CONTAINING SUCH AGENTS

DESCRIPTION

This invention relates to the production of carrier particles useful as carriers of proteins and other materials, such as enzymes, lectins and more particularly antigens and antibodies, used in agglutination tests, to producing diagnostic agents therefrom, and to test kits containing such agents.

It is well known that particulate materials of biological origin, especially erythrocytes, may be used as carriers. Erythrocytes have several properties which make them particularly useful in agglutination systems. They are readily available, are extremely uniform in size, and their agglutination is easy to see. Many antigens and antibodies can be attached to them without difficulty by simple procedures, e.g. by tanning or by reaction with glutaraldehyde. These factors, and the absence of suitable alternative carriers, help to explain the widespread use of erythrocytes in agglutination systems. However, erythrocytes are not free from disadvantages. Thus, they are rather unstable and do not always sediment satisfactorily. Stability may be improved by treatment with aldehydes such as glutaraldehyde, pyruvaldehyde and formaldehyde or with bifunctional imidoesters (e.g. dimethyl suberimidate) or carbodiimide. Unfavourable sedimentation behaviour in microtitre systems can be remedied to a considerable degree by supplementing the medium in which the test is conducted with appropriate additives, e.g. heterologous serum, or a wetting agent.

A further disadvantage of erythrocytes, as of some other known carrier particles, is caused by the presence of cellular antigens on their surface. These react with naturally-occurring antibodies in serum causing so-called 'non-specific' agglutination of the carrier particles. Several solutions to this problem of non-specific agglutination have been suggested. While the antigens cannot be removed from the erythrocytes without fundamental and undesirable change to them, there are compromise solutions. The most widely used of these is the provision of competitive antigens in solution in a liquid diluent. This method is not very efficient. One reason is that the serum antigens are not identical to the antigens on the surface of the erythrocyte. A second reason is that these antigens, even if isolated, generally have low chemical activity in aqueous solutions near to physiological pH and ionic strength. Thus, the problem of non-specific agglutination has not been entirely solved and limits the usefulness of erythrocytes in agglutination systems.

Synthetic carriers have been suggested as alternatives which might avoid some of the disadvantages of erythrocytes and other "natural" carriers, e.g. bacteria. Latex is an example of a synthetic carrier which has been used in slide agglutination procedures. However, it is not uniform in size unless it is graded carefully and it presents problems both with regard to the stable attachment of antigens and antibodies and the instability of the end-point. It is also prone to agglutination by serum lipid.

Although there are references in the literature to the use of yeast cells as carrier particles in agglutination tests, little practical attention appears to have been given to them. There would appear to be at least two major reasons for this. First it is well known that many human sera contain yeast agglutinins at high titre. Secondly, agglutination of yeast is not as easy to see as that of erythrocytes.

The present invention provides a process for producing carrier particles from yeast cells in a way which overcomes or at least reduces the problems of non-specific agglutination and poor visibility. This process comprises cross-linking the proteins in the yeast cell cytoplasm by reaction with a cross-linking agent, e.g. a dialdehyde, and stabilising the carbohydrate components of the yeast cell wall by reaction with an epihalohydrin or epoxide of low molecular weight.

Carrier particles produced from yeast cells in this way are particularly useful as carriers for diagnostic agents, viz. antigens (or antibodies) for the detection of antibodies (or antigens) in biological fluids, e.g. blood, serum, plasma, urine, but can also be used, for example, as carriers in enzyme immunoassay.

Baker's yeast, *Saccharomyces cerevisiae*, is very suitable as the starting material in this process and is readily available commercially as a stationary phase culture of uniform size distribution.

In the new process, the yeast cell cytoplasm is stabilised prior to manipulation and storage by treating the yeast, preferably in aqueous suspension, with agents which cross-link proteins and nucleic acids, and especially with dialdehydes, e.g. formaldehyde, (which is effectively a dialdehyde in this context) or glutaraldehyde. The treatment may be carried out at ambient temperature, e.g. 15° to 25° C., using 0.05 to 0.5 g of formaldehyde per gram of yeast cells at a pH of 6 to 8. The treatment is complete in 24 hours. Other aldehydes may be used in place of formaldehyde.

Before or after this treatment, the carbohydrate components of the yeast cell wall, especially the mannan, is stabilised by treatment with an epihalohydrin, e.g. epichlorohydrin, or other low molecular weight epoxide such as ethylene oxide or propylene oxide. In this way the mannan is rendered suitably stable during subsequent manipulation and storage. The treatment may be effected at ambient temperature, e.g. 15° to 25° C., using 2 to 20 grams of the epihalohydrin per gram of yeast cells. The reaction mixture is kept alkaline, e.g. with dilute sodium hydroxide solution and the reaction time is e.g. 10 minutes to 2 hours.

The invention provides two methods of reducing the interaction between antigenic sites, mainly mannan residues on the surface of the yeast cells, and serum agglutinins. These methods may be used either singly or in combination, depending on the demands of the situation, to minimize interference caused by nonspecific agglutination of the carrier of the diagnostic agents by normal human sera.

The first method involves incorporating a water-soluble mannose oligomer, and preferably a water-soluble extract of yeast cell walls (which is a convenient source of such an oligomer, i.e. of mannan) in the test system. The extract can be obtained by autoclaving an aqueous yeast suspension, treatment of the cells with acid or alkali or by extraction, e.g. with sodium dodecyl sulphate, deoxycholate or citrate buffer. After removal of particulate matter by centrifugation, mannan may be isolated from the reaction mixture after precipitation with Fehling's solution. A suitable method of extraction is described by Cifonelli J. A. and Smith F., J. Amer. Chem. Soc 77 5682 (1955). The mannan competes for the agglutinins. It is very soluble in aqueous solutions so that effective amounts can be incorporated as a basic component of a system useful in slide agglutination tests and microtitre plate tests for analysis of blood, serum or urine.

A second and preferred method involves chemical modification of cell wall antigens of the yeast so that they no longer react with serum antibodies. This can be done by treating yeast cells using esterification or etherification methods generally known in carbohydrate chemistry for blocking hydroxyl functions, e.g. acetylation, benzoylation, methylation, silylation or tetrahydropyranylation. For example, acetylation may be effected with acetic anhydride in pyridine at ambient temperature.

The chemical modification of cell wall antigens is conveniently done after stabilisation of the cell cytoplasm and stabilisation of the cell wall carbohydrate, and before or after, but preferably before, coupling of the antigen, antibody or other protein.

The carrier particles produced in accordance with the present invention may be dyed to make them readily visible. The yeast cells may be stained with a variety of dyes, for instance by mixing a dye solution with the yeast cell suspension and incubating the mixture at room temperature. It is preferred to use a reactive dyestuff. Examples of suitable dyes are basic fuchsin, fluorescein, fluorescein isothiocyanate, methyl violet and malachite green. Bifunctional dyes, such as those of the Procion M series (substances obtained by substitution of one chlorine of cyanuric chloride by a coloured molecule containing anionic solubilising groups) may also act as a coupling agent between cell wall and diagnostic agent.

Agglutination may be seen even in the presence of whole blood by using yeast cells stained with fluorescent dyes. If yeast cells are separately stained with two dyes and separately coupled to different antigens (or antibodies), more than one immunological system may be investigated concurrently on the same sample of blood. It is, of course, necessary that the dyes are distinguishable optically, e.g. basic fuschin and fluorescein which have distinct fluorescent spectra.

The present invention also provides procedures for attachment of antigens (or antibodies or other proteins or other materials used in agglutination tests) to the new carrier particles made from yeast cells. The diagnostic agents thus obtained are also a feature of the invention. In this Specification, the term "antigen" includes protein and carbohydrate antigens and simple chemical haptens. Lectins and enzymes may be attached to the carrier particles by similar methods.

The diagnostic agent, e.g. antigen, antibody, lectin or enzyme, is usually attached to residual carbohydrate, mostly either mannan, or substituted mannan, on the surface of the treated yeast cells. Attachment to cell walls proteins is not excluded, although they are not readily available on baker's yeast. Antigens or antibodies are therefore usually attached after activation of cell wall carbohydrate by reaction with a polyfunctional reagent which introduces reactive groups onto the cell surface.

Cyanuric chloride is suitable for this purpose. Examples of other suitable agents are cyanogen bromide, glutaraldehyde and carbodiimide.

Alternatively, the diagnostic agent may be attached to the yeast cells through bifunctional agents such as silane derivatives. The latter compounds have the advantage that they are effective at physiological pH and ionic strength. In some instances it may be advantageous to separate the diagnostic agent, e.g. antibody, from the yeast cell wall by a bifunctional spacer molecule, e.g. an alkylenediamine such as diaminohexane or aminoethanol. This can be introduced after activation of the surface of the treated yeast, e.g. by cyanuric chloride. Protein can be coupled to the alkylenediamine, e.g. with glutaraldehyde.

A preferred method of coupling the diagnostic agent to the treated yeast cells comprises treating the latter with 2 to 10 times their weight of cyanuric chloride in suspension in dioxane, washing the cells, and then reacting them with the diagnostic agent in aqueous suspension at ambient temperature and a pH of usually 4 to 6.

The order of the various treatment steps which are, or may be, involved in the present invention depends on the nature of the diagnostic agent and the methods used. Thus, modification of cell wall antigens by acetylation can proceed after the diagnostic agent has been attached. However, some antigens are affected adversely by the acetylation procedure so that in those cases acetylation should precede coupling of diagnostic agent. More generally, the steps should be carried out in such an order that no step interferes with any subsequent step, or vitiates the result of any preceding step.

Two major applications of carrier particles prepared from yeast cells by the new process are in (a) slide or tube agglutination tests and (b) microtitre tray tests.

(a) A suitable procedure for a slide test is as follows. 1 drop of serum at an appropriate dilution is placed on a microscope slide followed by one drop of a 1% suspension of coloured and sensitised yeast cells in physiological saline containing, when the antigenic sites of the cells have not been blocked, 50 mgml$^{-1}$ of mannan. The drops are mixed with a wooden applicator stick, the slide is rotated to ensure continuous mixing and the cells are examined for agglutination, which will be essentially at a maximum after 3 minutes. Thus yeast-human serum albumen (HSA) complexes could be detected, for example, with a rabbit anti-HSA serum at 1:1000 dilution with a microscopic end point.

Basic fuchsin or Procion MX are examples of dyes which give a clearly visible end-point in a slide test.

(b) A more sensitive and quantitative test is obtained if the test procedure is conducted in a microtitre plate. Here antigen (or antibody as appropriate) levels may be estimated by serial dilution of the test sample. The procedure is essentially similar to that in current practice with haemagglutination assays in microtitre plates and typically enables up to 100 samples to be processed concurrently. The reagent-sensitised yeasts are suspended at a concentration of 0.2% in a physiological buffer mixed with serial dilutions of the test sample and allowed to settle at room temperature in microtitre wells. In the negative reaction, cells settle to a button which is largely stable after 60 minutes. When agglutination occurs this is manifest by the formation of a distinctive mat in the microtitre well.

The chemical procedures used to modify the yeast cells, e.g. the aldehyde treatment, ensure sterile preparations if standard sterile technique is followed. The diagnostic agents have a long shelf life and may be stored for months in buffers of physiological pH at 4° C.

Alternatively, they may be lyophilised and reconstituted with buffer before use.

Yeasts prepared and used according to the present invention are suitable for the detection of antigens (or antibodies) in biological fluids e.g. serum, urine and whole blood. They can be used to prepare diagnostic agents or test kits based on such agents, to be employed in slide tests or microtitre systems using direct or inhibition agglutination principles. Test kits comprising a water-soluble mannose oligomer, and especially a water-soluble extract of yeast cell walls and at least one diagnostic agent, as hereinbefore described, are another feature of the invention.

The yeast cells treated in accordance with the present invention have the following advantages as carrier particles:

(a) The treated yeast cells have (when the surface hydroxyls have been blocked) low activity towards the antibodies found in high incidence in normal sera which agglutinate normal untreated yeasts.

(b) Treated yeast cells can be prepared sterile with a long shelf life under normal storage conditions, e.g. lyophilised or as a refrigerated suspension in physiological saline with added preservative.

(c) Treated yeast cells are of a suitable size and density, which contributes to the reproducibility of the preparations and appropriate sedimentation behaviour in agglutination systems including microtitre plates.

(d) Antigens and antibodies are readily attached to the yeast carrier.

(e) Treated and stained yeast cells are easily seen and agglutination is readily detected in either slide or microtitre systems by workers with little experience. This contributes to high sensitivity and reproducible results.

(f) Preparations can be made available in a range of colours allowing systems to be colour coded.

(g) Two or more antigen (and antibody) systems may be investigated concurrently using the same sample which may be whole blood. This is possible through use of detector carriers bearing different antigens in admixture, which carriers have been separately stained with fluorescent dyes of distinct emission spectra.

(h) Treated yeasts are suitable for use in either serum, urine or other biological fluids, such as plasma, or cerebrospinal fluid.

The following Examples illustrate the invention.

EXAMPLE 1

(a) Fixation of yeast cytoplasm with aldehyde 500 ml of a 50% suspension of baker's yeast *Saccharomyces cerevisiae* (Gist-Brocades, G.B., Ltd.) in phosphate-buffered saline (PBS, 20 mM potassium phosphate, pH 7.2 in 0.14 M sodium chloride) were stirred with 25 ml formaldehyde solution (1 part of 38% aqueous formaldehyde, i.e. formalin, added to 2 parts PBS) for 24 hours at 21° C. The cells were recovered by centrifugation, washed in PBS, suspended in PBS and adjusted to pH 7.6 with 10% ammonium hydroxide, washed by centrifugation in PBS and suspended at 50% in PBS.

In a similar way, yeast cells can be treated with 1% glutaraldehyde solution instead of the formaldehyde solution. Excess aldehyde is then removed by washing with 1% β-aminoethanol solution.

(b) Fixation of yeast carbohydrate with epichlorohydrin 15 ml of a 30% suspension of yeast cells in PBS, prepared in the manner just described, were added to 20 ml of 1 N sodium hydroxide solution and 25 ml of epichlorohydrin. The mixture was stirred rapidly at 21° C. for 30 minutes. The treated cells were then washed once with 30% ethanol-PBS and a further six times with PBS using centrifugation.

EXAMPLE 2

Concurrent fixation and staining of yeast

The procedure of Example 1(a) was followed, except that a staining solution was added with the formalin. This contained 32 ml methanol, 0.5 ml glacial acetic acid, 3 ml water and 50 mg basic fuchsin. Similar procedures were found suitable for other dyes, e.g. fluorescein isothiocyanate or rhodamine isothiocyanate.

EXAMPLE 3

Staining of yeast cells with Procion M dyes

Yeast cells treated as in Example 1(b) were suspended at a concentration of 25% in 1.25 M sodium carbonate solution and stirred with 2 volumes of a solution of Procion M dye in water at a concentration of 5 mg ml$^{-1}$ for 60 minutes at 23° C. Excess dye was removed by washing the cells by centrifugation in PBS. The rate of dye uptake was dependent on the particular dye. The following dyes of the Procion M type were readily coupled.

Yellow MX—8G
Orange MX—G
Scarlet MX—G
Blue MX—3G

EXAMPLE 4

Acetylation of yeast cells

A suspension of yeast cells prepared as described in Example 1 was suspended at a concentration of 2.5% in pyridine:acetic anhydride (1:1) and the mixture was stirred at room temperature for 3 hours and centrifuged, washed in C.2 M sodium acetate buffer, pH 5.0. The yeast was recovered by centrifugation and washed to pH 7.2 in PBS.

In a similar way, the cells treated according to Example 2 or 3 may be acetylated.

EXAMPLE 5

Coupling of antigens and antibodies to yeast with cyanogen bromide 2 ml of a 1% yeast cell suspension prepared as in any of the Examples 1, 2 and 3, were added to 7 ml 0.2 M potassium phosphate buffer, pH 10.5, followed by an equal volume of water containing 0.5 g cyanogen bromide, and the mixture was stirred at 10° C. for 7 minutes. The pH was kept constant by addition of 1 N sodium hydroxide. The treated cells were separated and washed twice in 0.1 M sodium bicarbonate at 4° C. They were then resuspended with brief sonication in 0.5 ml PBS containing 25 μg HBs antigen of hepatitis B, trace labelled with 125 I HBs. After stirring at 4° C. for 18 hours, the yeast cells were separated and washed by centrifugation (3X) in PBS containing 10 mM EDTA and 0.25% gelatin. They were then resuspended at a concentration of 0.5% in the same buffer mixture with brief sonication. Approximately 95% of the antigen protein was found to be coupled to the yeast cells.

By using the same procedure, but substituting antibodies to Ig G or hepatitis B virus in amounts ranging from 10 to 100 μg, the corresponding antigens were also coupled efficiently.

EXAMPLE 6

Coupling of peroxidase to yeast with triethoxysilane

3-Aminopropyltriethoxysilane (1 ml) and 1.8 ml of 0.1% acetic acid were made up to 10 ml with water and added to 0.4 g sedimented yeast cells, which had been produced as described in Example 1. The mixture was stirred at room temperature for 24 hours and the cells were then separated and washed thoroughly with water. A 1% suspension of the treated cells in PBS, containing 5% glutaraldehyde was added to 2.5 mg of horseradish peroxidase in 2.5 ml PBS and kept at 21° C. for one hour. The cells were then separated and washed with PBS by centrifugation.

EXAMPLE 7

Fixation of protein to yeast with cyanuric chloride 10 ml of a 1% suspension of yeast cells prepared as in Example 1 were suspended in 1 N NaOH for 30 minutes at 21° C. After separation by centrifugation, the yeast cells were suspended at a concentration of 1% in dioxane containing 50 mg ml$^{-1}$ cyanuric chloride and kept for 30 minutes at 21° C. with stirring. The cells were separated and washed by centrifugation sequentially in dioxane/water mixtures containing 70%, 50%, 25% and 10% dioxane respectively. The cells were finally resuspended at 5% in 50 mM sodium acetate solution of pH 5.0. Protein at 20–500 μg ml$^{-1}$ was then added in PBS to the suspension and the mixture was kept for 30 minutes at 21° C. with stirring. The treated cells were finally washed by centrifugation, 6x with 2 M NaCl and 2x with PBS.

The protein used in this Example may be, for example, IgG antibodies to e.g., human IgG or lactoperoxidase.

EXAMPLE 8

Reaction of acetylated yeast with concanavalin A and antimannan antibodies

Slide tests were performed with yeast cells prepared as described in Example 1 with concanavalin A solution (10 μg ml$^{-1}$) and serum (1:1000) showing a high titre of antibodies to mannan. In all cases agglutination was observed. The tests were also performed using acetylated cells as described in Example 4. The cells did not give detectable reactions with concanavalin A up to 500 μg ml$^{-1}$ or with 1:2 dilutions of the serum.

EXAMPLE 9

Estimation of serum antibodies to hepatitis B surface antigen (HBs)

Rabbit antibody to HBs was coupled to yeast cells as described in Example 5 or 7, and the yeast cells were suspended in 0.2% GES buffer. Serial dilutions of sera to be tested for antigen were made in GES and added (25 μl) to the wells of 'V'-bottomed microtitre plates (Linbro). 25 μl mannan (50 mg ml$^{-1}$) in GES and 25 μl of yeast cell suspension were then added and mixed. The test was read against an illuminated background after standing 90 minutes at room temperature. Agglutination was shown by cells being spread out over the bottom of the well.

A negative result was shown by cells settling to a tight button. Sera were assayed in parallel for antibody to HBs by radioimmunoassay (Heathcote, Cameron and Dane, Lancet 1974 (i) page 71). Sera showing high titre by radioimmunoassay showed agglutination at dilutions up to 1:40,000. This was against a background of nonspecific agglutination with normal human sera at dilutions up to 1:64.

I claim:

1. Process for the production of carrier particles from yeast cells which comprises cross-linking the proteins in the cell cytoplasm by reaction with a cross-linking agent and stabilizing the carbohydrate components of the yeast cell wall by reaction with an epihalohydrin or other low molecular weight epoxide.

2. Process according to claim 1 in which the said cross-linking agent is formaldehyde or glutaraldehyde.

3. Process according to claim 1 in which the said epihalohydrin is epichlorohydrin.

4. Process according to claim 1 in which the said yeast cells are also dyed.

5. Process according to claim 4 in which the cells are dyed with a reactive dyestuff.

6. Process according to claim 4 in which the cells are dyed with a fluorescent dyestuff.

7. Process according to claim 1 in which the cells are treated so as to block the hydroxyl functions in the cell wall carbohydrates.

8. Process according to claim 7 in which the said hydroxyl functions are esterified or etherified.

9. Process according to claim 8 in which the said hydroxyl functions are acetylated, benzoylated, methylated, tetrahydropyranylated, or silylated.

10. Process for the production of a diagnostic reagent which comprises coupling yeast cells with an antibody, antigen, enzyme or lectin at any stage during a process as defined in claim 1, 4 or 7.

11. Process according to claim 10 in which the coupling takes place after the cross-linking of the proteins in the cell wall, the stabilization of the carbohydrate in the cell wall, and any optional dyeing of the yeast cells but before any optional treatment to block the hydroxyl functions of the cell wall carbohydrate.

12. Process according to claim 10 in which the coupling takes place after the cross-linking of the proteins in the cell wall, the stabilization of the carbohydrate in the cell wall, the treatment to block the hydroxyl functions of the cell wall carbohydrate, and any optional dyeing of the yeast cells.

13. Process according to claim 10 in which the yeast cells are first activated by reaction with cyanuric chloride and then coupled to the antibody, antigen, enzyme, or lectin by reaction of the activated cells therewith.

14. Process according to claim 10 in which the yeast cells are first activated by reaction with cyanogen bromide and then coupled to the antibody, antigen, enzyme or lectin by reaction of the activated cells therewith.

15. A test kit which comprises a water-soluble mannose oligomer and at least one diagnostic agent produced by the process of claim 10.

16. A test kit which comprises a water-soluble extract of yeast cell walls and at least one diagnostic agent produced by the process of claim 10.

17. Stabilized carrier particles produced by the process of claim 1.

18. A diagnostic reagent produced by the process of claim 10.

* * * * *